(12) United States Patent
Altrogge et al.

(10) Patent No.: US 11,661,595 B2
(45) Date of Patent: May 30, 2023

(54) DEVICE AND METHOD FOR LARGE VOLUME TRANSFECTION

(71) Applicant: Lonza Cologne GmbH, Cologne (DE)

(72) Inventors: Ludger Altrogge, Metternich (DE); Timo Gleissner, Euskirchen (DE); Andreas Heinze, Cologne (DE); Sven Hermsmeier, Bonn (DE)

(73) Assignee: Lonza Cologne GmbH, Cologne (DE)

( * ) Notice: Subject to any disclaimer, the term of this patent is extended or adjusted under 35 U.S.C. 154(b) by 63 days.

(21) Appl. No.: 16/820,847

(22) Filed: Mar. 17, 2020

(65) Prior Publication Data

US 2020/0325466 A1 Oct. 15, 2020

Related U.S. Application Data

(62) Division of application No. 15/308,366, filed as application No. PCT/EP2015/059152 on Apr. 28, 2015, now Pat. No. 10,633,646.

(30) Foreign Application Priority Data

May 2, 2014 (EP) .................................... 14166918
Oct. 31, 2014 (EP) .................................... 14191272

(51) Int. Cl.
*C12N 13/00* (2006.01)
*C12M 3/00* (2006.01)
(Continued)

(52) U.S. Cl.
CPC ........... *C12N 13/00* (2013.01); *A61N 1/0412* (2013.01); *C12M 35/02* (2013.01); *C12N 15/87* (2013.01)

(58) Field of Classification Search
CPC ....... C12M 35/00; C12M 35/02; C12M 35/04
See application file for complete search history.

(56) References Cited

U.S. PATENT DOCUMENTS 5,563,067 A 10/1996 Sugihara et al.
5,810,725 A 9/1998 Sugihara et al.
(Continued)

FOREIGN PATENT DOCUMENTS

WO 2004083379 A2 9/2004
WO 2005113820 A2 12/2005
(Continued)

OTHER PUBLICATIONS

S.M. Kennedy et al.: "Quantification of Electroporative Uptake Kinetics and Electric Field Heterogeneity Effects in Cells", Biophysical Journal, vol. 94, No. 12, Jun. 1, 2008, pp. 5018-5027, XP055166631.

*Primary Examiner* — Nathan A Bowers
(74) *Attorney, Agent, or Firm* — Agris & Von Natzmer, LLP; Joyce Von Natzmer

(57) ABSTRACT

Disclosed is a device for applying an electric field to a suspension of cells, comprising at least one chamber which comprises at least one internal space (40) for holding the suspension, the internal space (40) comprising at least two segments (41, 42), wherein each segment (41, 42) comprises at least one electrode (43, 44) and wherein neighboring electrodes (43, 44) are separated from each other by at least one gap (47) which is at least partially filled with an insulating material (46), and wherein the edges of the electrodes (43, 44) facing each other within the internal space (40) are rounded. Rounding the electrodes' edges facing a neighboring electrode results in a significant reduction of field gradients and thus even of the risk of arcing. Also disclosed is a method in which voltage is applied to at least one active electrode (43, 44) while the electrodes (43, 44, 45) or electrode segments next and/or opposite to the active electrode (43, 44) are set to ground potential. Setting neighboring electrodes that surround the active electrode to ground potential results in decreased scattering of the electric field within the internal space so that the electrically active area is locally limited and the field lines are focused near the active electrode and thus control of the process is enhanced.

13 Claims, 13 Drawing Sheets

(51) Int. Cl.
  *B01L 3/00*   (2006.01)
  *C12M 1/42*   (2006.01)
  *C12N 15/87*  (2006.01)
  *A61N 1/04*   (2006.01)

(56) References Cited

U.S. PATENT DOCUMENTS

| | | |
|---|---|---|
| 6,150,148 A | 11/2000 | Nanda et al. |
| 6,169,394 B1 | 1/2001 | Frazier et al. |
| 6,653,136 B1 | 11/2003 | Dodgson et al. |
| 2005/0070018 A1* | 3/2005 | Johnson ................. C12M 35/02 435/461 |
| 2007/0128708 A1 | 6/2007 | Gamelin |
| 2007/0155015 A1* | 7/2007 | Vassanelli .............. C12N 15/87 435/461 |
| 2007/0243634 A1* | 10/2007 | Pamula ................. C12Q 1/686 436/518 |
| 2010/0307917 A1 | 12/2010 | Srinivasan et al. |
| 2013/0146459 A1 | 6/2013 | Bazant et al. |
| 2013/0260434 A1 | 10/2013 | Mueller-Hartmann et al. |

FOREIGN PATENT DOCUMENTS

| | | | |
|---|---|---|---|
| WO | 2007120234 | A2 | 10/2007 |
| WO | 2011161092 | A1 | 12/2011 |

\* cited by examiner

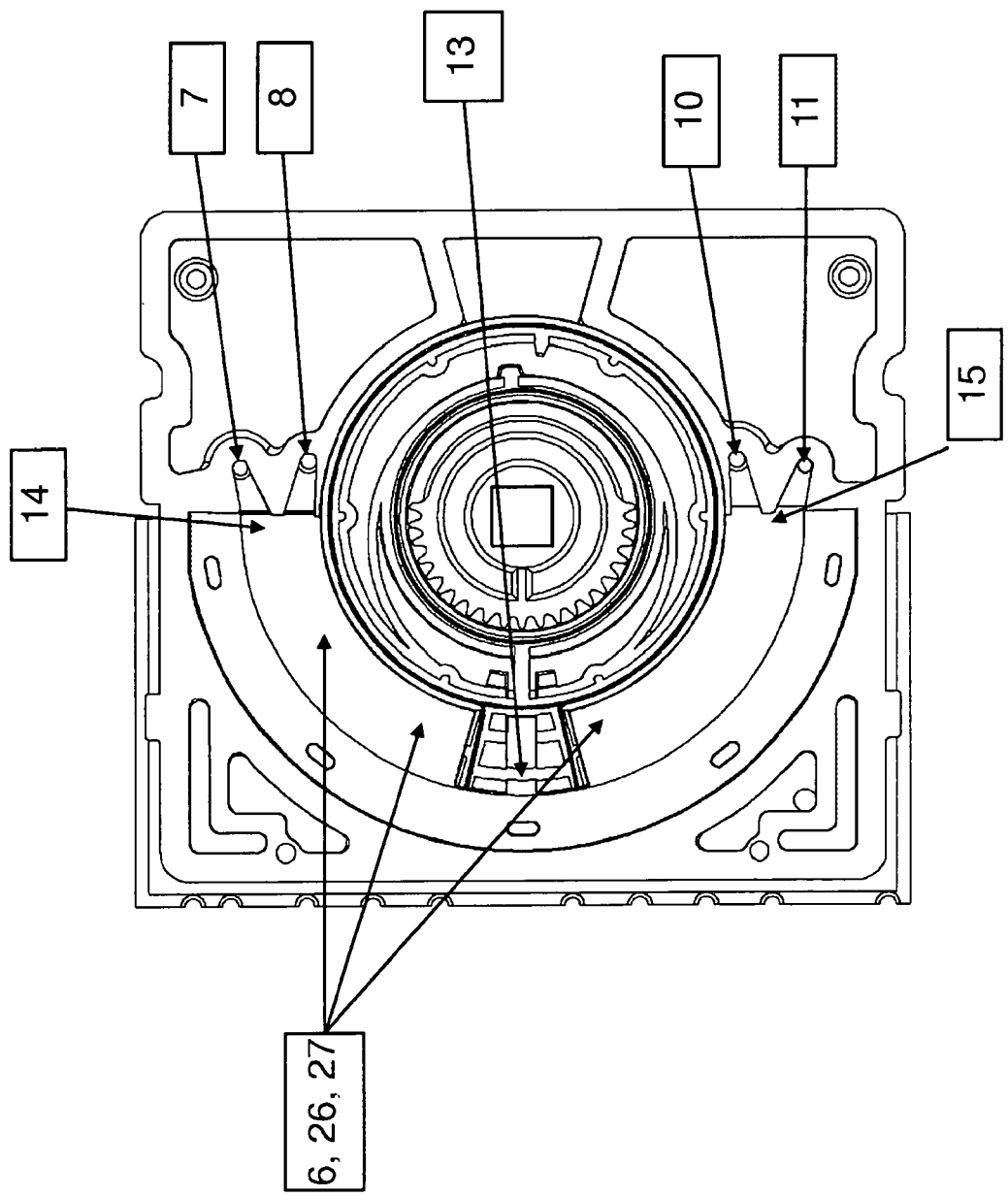

DEVICE AND METHOD FOR LARGE VOLUME TRANSFECTION

CROSS-REFERENCE TO RELATED APPLICATIONS

This is a divisional application of the U.S. application Ser. No. 15/308,366, filed Nov. 2, 2016, which is a national stage of International application PCT/EP2015/059152, filed Apr. 28, 2015 designating the United States, which are incorporated herein by reference in their entireties, and claims priority to European application EP 14166918.4, filed May 2, 2014 and to European application EP 14191272.5, filed Oct. 31, 2014.

BACKGROUND OF AND INTRODUCTION TO THE INVENTION

The invention relates to a device for applying an electric field to a suspension of cells, cell derivatives, organelles, sub-cellular particles and/or vesicles, comprising at least one chamber which comprises at least one internal space for holding the suspension, the internal space comprising at least two segments, wherein each segment comprises at least one electrode and wherein neighboring electrodes are separated from each other by at least one gap which is at least partially filled with an insulating material. The invention further concerns a method for applying an electric field to a suspension of cells, cell derivatives, organelles, sub-cellular particles and/or vesicles, wherein a voltage is applied to electrodes of a chamber comprising at least one internal space for holding the suspension, the internal space comprising at least two segments, wherein each segment comprises at least one electrode.

The introduction of biologically active molecules, for example DNA, RNA or proteins, into living cells, cell derivatives, organelles, sub-cellular particles and/or vesicles may, e.g., serves to examine the biological functions of these molecules and is, moreover, an essential precondition for the success of the therapeutic use of these molecules, e.g., in gene therapy. A preferred method for introducing external molecules into the cells is called electroporation, which unlike chemical methods limits undesirable changes in the structure and function of the target cell. In electroporation the external molecules are introduced into the cells from an aqueous solution, preferably a buffer solution specifically adapted to the cells, or a cell culture medium, via a short current flow, i.e., e.g., the pulse of a discharging capacitor which renders the cell membrane transiently permeable to the external molecules. The temporary "pores" that are formed in the cell membrane allow the biologically active molecules to first reach the cytoplasm in which they may already perform their function or exert any therapeutic action to be examined, and then, under certain conditions, to also reach the cell nucleus as it is required, e.g., in gene therapy applications.

Due to a short application of a strong electrical field, i.e. a short pulse with a high current density, cells, cell derivatives, organelles, sub-cellular particles and/or vesicles may also be fused. In this so-called electrofusion the cells are, e.g., initially brought into close membrane contact by an inhomogeneous electrical alternating field. The subsequent application of an electrical field pulse leads to interaction between membrane parts, which ultimately results in fusion. Devices comparable to those used for electroporation may be used for electrofusion as well.

Smaller volumes of suspension of cells, cell derivatives, organelles, sub-cellular particles and/or vesicles are generally treated in a batch process in relatively simple vessels. The solution or cell suspension, respectively, is frequently located in a cuvette, i.e. a narrow vessel open at the top, which in the vicinity of the bottom has two opposing, parallel electrodes in the lateral walls which serve to apply the electrical voltage. However, such vessels are unsuitable for treating larger volumes as the reaction space available for the electrical treatment is limited by the limited maximal distance between the electrodes. Thus, flow-through processes in which the cell or vesicle suspension is continuously or discontinuously fed through the reaction space between the electrodes are often used for the electroporation or electrofusion of larger volumes.

WO 2011/161092 A1 discloses an electrode assembly for applying an electric field to adherent cells growing at the bottom of a container. The electrode assembly is designed to be inserted into the container and comprises a plurality of electrodes, each having a surface which is arranged opposite the corresponding surface of the next electrode. The gap between these surfaces is completely filled with an electrically insulating material so that the electric field is concentrated in the region of the cells to be treated such that a voltage pulse, or the current produced thereby, flows through the cells.

US 2007/0128708 A1 discloses a scalable device for electroporating relatively large volumes of a fluid medium carrying biological cells or vesicles in a segmented chamber, wherein each segment comprises two electrodes. The effective volume of the chamber can be varied by moving a plunger along the longitudinal axis of the chamber. Thus, the volume chosen is directly related to the volume of the sample to be electroporated. The sample is sucked in and purged out of the chamber through a port disposed in the end wall of the chamber. The sample within the chamber is processed by sequentially applying voltage pulses to the electrode pairs of the individual segments of the chamber.

However, it is a drawback of the prior art devices and methods that the risk of arcing is increased, especially if high voltages are applied to segmented electrodes, and that the electric field lines can spread out into regions aside the active electrode segment(s).

It is therefore an object of the invention to provide a device and a method for treating cells, cell derivatives, organelles, sub-cellular particles and/or vesicles, with segmented electrodes for keeping electrical currents low, and with which the risk of arcing is reduced and the electric field is confined to the region near the active electrode segment(s).

SUMMARY OF THE INVENTION

The object is met by a device for applying an electric field to a suspension of cells, cell derivatives, organelles, sub-cellular particles and/or vesicles as initially specified, with which the edges of the electrodes facing each other within the internal space are rounded. If voltage is applied to the electrodes, the risk of arcing is significantly increased in regions of sharp contour changes (edges) or if inhomogeneity of the electric field occur very close to the electrode surface of an active segment. Surprisingly, rounding the electrodes' edges facing a neighboring electrode results in a significant reduction of such field gradients and thus even of the risk of arcing. According to the invention, homogenization of the electric field within the internal space of the chamber and especially near the electrode surface in the region of the gaps between electrode segments is achieved by the provision of a smooth shape transition from a first electrode surface facing the lumen of the internal space to a second electrode surface perpendicular to the first electrode surface, whereby the second electrode surface is facing the electrode gap. In particular the smooth shape transition is provided by a curved electrode surface, i.e. from a larger to a smaller fillet radius (e.g. several tangentially linked circle segments or a spline).

Moreover, reduction of field gradients and homogenization of the electric field also results in decreased scattering of the electric field within the internal space. Accordingly, the rounded edges of the electrodes facing each other within the internal space of the chamber have the surprising effect that high field densities are avoided.

According to an exemplary embodiment of the invention the fillet radius of the rounded edges of the electrodes is maximized. Surprisingly, it has been found out that reducing the inhomogeneity of the electric field by maximizing the fillet radius of the rounded edges results in a significant decrease of the likelihood of arcing. That is, the larger the radius of the rounded edges, the lower the risk of arcing.

In another exemplary embodiment of the invention the width of the gap and/or the distance between two neighboring electrodes is minimized. As the cells, cell derivatives, organelles, sub-cellular particles and/or vesicles are not sufficiently processed in the internal space around the gap, the gap (i.e. the distance between two neighboring electrodes) should be as small as possible.

Accordingly, the smaller the width of the gap, the higher the efficiency of processing.

For example, the design of the device according to the invention can be optimized by determining the optimal ratio of fillet radius and gap width. That is, the fillet radius of the rounded edges of the electrodes has to be maximized while the width of the gap has to be minimized. The ideal design ensures a very low risk of arcing and a very high processing efficiency.

In an exemplary embodiment, which is suitable for many applications, the fillet radius of the rounded edges of at least one of the electrodes is in the range of about 0.3-2.0 mm. For example, the radius may be in the range of about 0.3-1.8, 0.3-1.6, 0.3-1.4, 0.3-1.2, 0.3-1.0, 0.5-2.0, 0.7-2.0, 0.9-2.0, 1.0-2.0, 0.4-1.9, 0.5-1.8, 0.6-1.7, 0.7-1.6, 0.8-1.5, 0.9-1.4, or 1.0-1.2.

In the same or another exemplary embodiment, which is also suitable for many applications, the width of the gap and/or the distance between two neighboring electrodes is in the range of about 0.5-2.0 mm. For example, the width may be in the range of about 0.5-1.8, 0.5-1.6, 0.5-1.4, 0.5-1.2, 0.5-1.0, 0.6-2.0, 0.7-2.0, 0.9-2.0, 1.0-2.0, 0.6-1.9, 0.7-1.8, 0.8-1.7, 0.9-1.6, 1.0-1.5, 1.1-1.4, or 1.1-1.3.

In another exemplary embodiment of the invention the surface of the insulating material facing the internal space miters the surface of at least one electrode in a right angle. By designing the surface of the insulating material such that it is arranged perpendicular to the electrode's surface, the equipotential lines of the electric field meet the surface of the electrode orthogonally and are not deflected. As a result, remaining inhomogeneity of the electric field can be avoided within the chamber or at least moved to a region within the insulating material or away from the electrode surface of the active segment so that the likelihood of arcing is further reduced. Moreover, the maximum field density close to the active electrode is decreased.

In the same or another exemplary embodiment the design of the device according to the invention can be optimized by varying the radii for the curvature of the electrodes in order to maximize the radius of the electrode surface facing the lumen of the internal space of the chamber and at the same time minimizing the gap width. That is, in an exemplary embodiment the radius of the electrode surface facing the lumen of the internal space can be larger than the radius of the electrode surface facing the insulating material of the gap.

In particular, in an exemplary embodiment the radius of the electrode surface facing the lumen of the internal space is in the range of about 1.0-2.0 mm, and the radius of the electrode surface facing the insulating material of the gap is in the range of 0.3-2.0 mm. As a further aspect of this embodiment the surface of the insulating material facing the internal space miters the surface of at least one electrode in a right angle exactly at or in the vicinity of the position of the radius change of the electrode surface curvature.

The insulating material within the gap between two neighboring electrodes may, for example, comprise or consist of polycarbonate.

In another exemplary embodiment of the invention at least one of the electrodes is larger than the other(s). For example, the larger electrode may be a counter or ground electrode that is arranged opposite to the smaller electrodes. In this embodiment the smaller electrodes can be either active electrodes that are set to high voltage or electrodes that are set to ground potential.

In an exemplary embodiment, which is suitable for many applications, at least one electrode has a width in the range of 5-20 mm and at least one electrode has a width in the range of 20-80 mm.

In another exemplary embodiment of the invention the gap is arranged such that a part of at least one electrode is disposed opposite to said gap. Since in this advantageous arrangement each gap is not arranged opposite to another gap but instead opposite to an electrode, the regions within the internal space of the chamber which are not exposed to an electric field sufficient for efficient processing are minimized or even eliminated. As a result, the overall processing efficiency is effectively increased by this measure.

In yet another exemplary embodiment of the invention each segment is provided with at least one first electrode and at least one second electrode, wherein the second electrode is a common electrode of at least two segments. Such configuration facilitates construction and assembly of the device according to the invention and further avoids complicated wiring.

For example, the chamber of the device according to the invention may comprise corresponding components which can be attached to each other. That is, the device according to the invention can be assembled, e.g., by attaching two components to each other, wherein each component comprises a recess that corresponds to the recess of the other component. If these two components are attached to each other, their aligned recesses form the internal space of the chamber. In order to be capable of producing an electric field within the internal space, each recess can be provided with at least one electrode. At least some of the electrodes may be segmented. For example, one half of the electrodes (at one side of the symmetry axis) can be segmented while the other half of the electrodes (at the other side of the symmetry axis) can be a single, unsegmented electrode which may be used as a counter electrode. In an advantageous embodiment the two components are identical so that cost-effective production is ensured. As the identical components are rotationally symmetric, easy assembly by attaching the components to each other is ensured.

In an exemplary embodiment of the invention at least one segment has a volume in the range of about 10 μl to 500 μl or 20 μl to 400 μl or 30 μl to 300 μl or 50 μl to 200 μl.

In the same or another exemplary embodiment the lumen of the internal space of the chamber has a volume of at least 500 μl or at least 800 μl or at least 1 ml.

The invention further relates to a method for producing a device for applying an electric field to a suspension of cells, cell derivatives, organelles, sub-cellular particles and/or vesicles, for example, the device according to the invention as described above, wherein at least one chamber is provided, which comprises at least one internal space for holding the suspension, the internal space comprising at least two segments and each segment comprising at least one electrode, wherein an insulating material is at least partially filled into at least one gap which separates neighboring electrodes from each other, and wherein the edges of the electrodes facing each other within the internal space are machined such that they are rounded. Due to this advantageous design, the risk of arcing if voltage is applied to the electrodes is significantly reduced.

According to an exemplary embodiment of this method the fillet radius of the rounded edges of the electrodes is maximized. In another exemplary embodiment of the method the width of the gap and/or the distance between two neighboring electrodes is minimized. For example, the design of the device according to the invention can be optimized by determining the optimal ratio of fillet radius and gap width. That is, the fillet radius of the rounded edges of the electrodes has to be maximized while the width of the gap has to be minimized. The ideal design ensures a very low risk of arcing and a very high processing efficiency.

In another exemplary embodiment of the method the surface of the insulating material facing the internal space is formed such that it miters the surface of at least one electrode in a right angle. By forming the surface of the insulating material such that it is arranged perpendicular to the electrode's surface, the equipotential lines of the electric field meet the surface of the electrode orthogonally and are not deflected. As a result, remaining inhomogeneity of the electric field can be avoided within the chamber or at least moved to a region within the insulating material and/or away from the active electrode surface so that the likelihood of arcing is further reduced. Moreover, the maximum field density close to the active electrode is decreased.

In yet another exemplary embodiment of the invention at least one of the electrodes integrated in the device is larger than the other(s). For example, the larger electrode may be used as a counter or ground electrode that is arranged opposite to the smaller electrodes. In such embodiment the smaller electrodes can be either used as active electrodes that are set to high voltage or as electrodes that are set to ground potential. In this embodiment each segment can be provided with at least one first electrode and at least one second electrode, wherein the second electrode is a common electrode of at least two segments. Such configuration facilitates construction and assembly of the device according to the invention and further avoids complicated wiring during production of the device.

In yet another exemplary embodiment of the invention the gap is arranged such that a part of at least one electrode is disposed opposite to said gap. Since in this advantageous arrangement each gap is not arranged opposite to another gap but instead opposite to an electrode, the regions within the internal space of the chamber which are not exposed to an electric field sufficient for efficient processing are minimized or even eliminated. As a result, the overall processing efficiency is effectively increased by this measure.

The object is further met by a method for applying an electric field to a suspension of cells, cell derivatives, organelles, sub-cellular particles and/or vesicles as initially specified, wherein the voltage is applied to at least one active electrode while the electrodes or electrode segments next and/or opposite to the active electrode are set to ground potential. Setting the neighboring electrodes that surround the active electrode to ground potential results in decreased scattering of the electric field within the internal space so that the electrically active area is locally limited and the field lines are focused near the active electrode and thus control of the process is enhanced, especially if large volumes are processed in a segmented chamber.

In an exemplary and advantageous embodiment of the invention the voltage is applied to only one active electrode while all other electrodes or electrode segments in the internal space are set to ground potential. Setting all electrodes in the internal space of the chamber, but for the active electrode, to ground potential ensures that the field lines are focused in the internal space near the active electrode and thus only in the active segment of the chamber and locally faded out towards the neighboring electrodes.

In another exemplary embodiment of the invention the voltage is applied to at least two electrodes or electrode segments in the internal space sequentially. It is an advantage of the invention that each segment of the internal space of the chamber can be electrically addressed individually so that controlled generation of electric fields within the chamber can be precisely achieved. For example, in order to avoid arcing and/or undesired heating of the suspension, voltage pulses can be applied to different segments sequentially. To this end, each segment is provided with at least one electrode which can be individually addressed so that voltage pulses can be applied to the segments of a chamber in sequence.

For example, the segment closest to an outlet port of the chamber is processed as first segment followed by the neighboring segment until the last segment in this sequence, the segment most distant to the outlet port, is being processed. That is, the voltage is at first applied to the segment closest to an outlet port of the chamber, followed by the neighboring segment until the voltage is applied to the last segment in this sequence, the segment most distant to the outlet port. In this exemplary embodiment of the invention the segment closest to the outlet port is processed as first segment followed by the neighboring segment until the last segment in this sequence, the segment most distant to the outlet, is being processed. This processing sequence makes sure that gas bubbles occurring during the application of a high voltage to the cell suspension do not push unprocessed samples towards and/or out of the outlet but processed sample only.

In yet another exemplary embodiment of the invention each segment is provided with at least one first electrode and at least one second electrode, wherein the voltage is applied to the first electrode and the second electrode is a common electrode of at least two segments. Accordingly, the number of electrodes in the internal space of the device can be significantly reduced so that control of the process is facilitated.

The term "rounded" as used herein refers to a curved and even surface wherein the shape transition from a flat region to another flat region is tangential.

The term "active electrode" as used herein refers to an electrode to which a voltage is applied but which is not set to ground potential. For example, an "active electrode" may be an electrode which is set to high voltage potential.

The term "electrode segment" as used herein refers to a separate part of a segmented electrode, i.e. an electrode which is divided into different parts, wherein the separate parts of the segmented electrode are not electrically coupled to each other.

The term "segment" as used herein refers to an area of the internal space of a chamber, which comprises at least one electrode or electrode segment.

The term "active segment" as used herein refers to a segment of a chamber, which comprises at least one active electrode.

The invention is further exemplarily described in detail with reference to the figures.

DESCRIPTION OF VARIOUS AND PREFERRED EMBODIMENTS

Figure 1A:
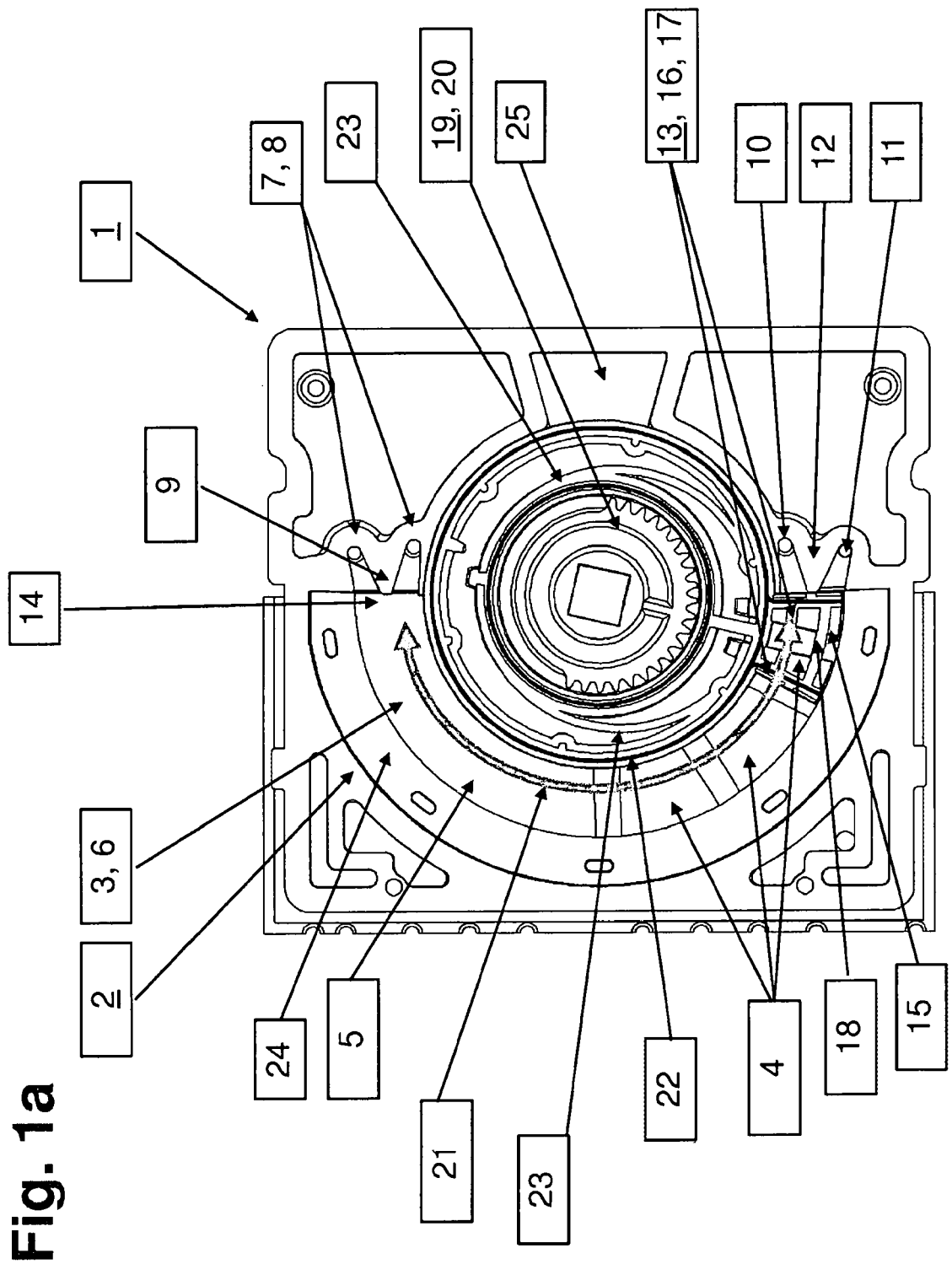
FIG. 1 shows an exemplary embodiment of an individual component of a device according to the invention comprising a rotatable adjusting means and a curved chamber design.
  a) Separating element in a position at a lower terminal point
  b) Separating element in an intermediate position
Figure 1B:
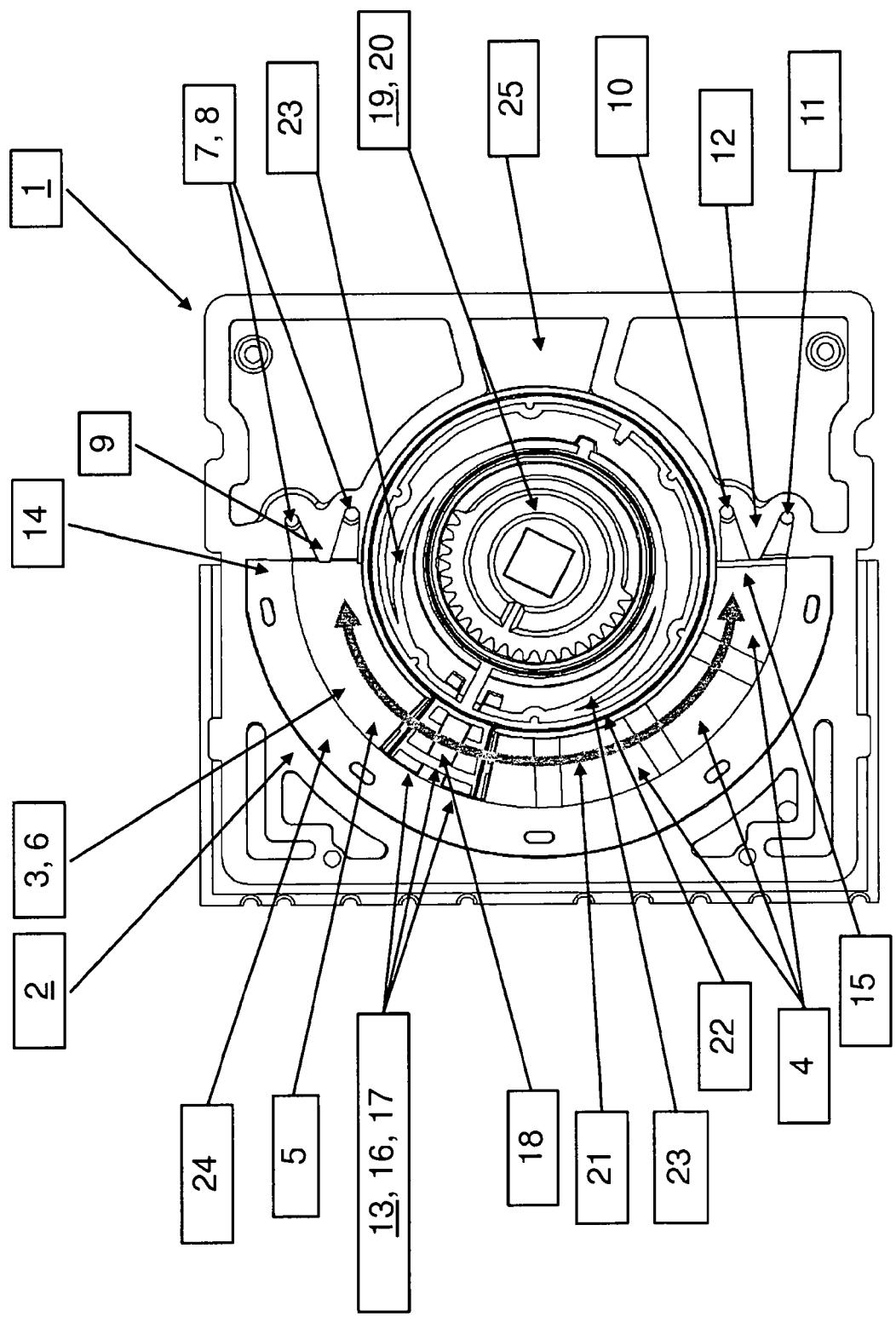

FIGS. 1a and 1b show an exemplary embodiment of an individual component of a device 1 according to the invention. The device 1 comprises a base member 2 having a curved recess 3 which is provided with four electrodes 4, 5. Three of these electrodes are segment electrodes 4 while one electrode is a counter electrode 5. The base member 2 represents one component of the device 1 which is assembled of two components that are attached to each other, wherein at least the inner sides of these components are identical. That is, the base member 2 and a second base member (base member 30 shown in FIG. 3) having an identical inner side are attached to each other so that the recess 3 and a corresponding recess of the second base member form a chamber 6 for holding a suspension of cells, cell derivatives, organelles, sub-cellular particles and/or vesicles. In this chamber 6 an electric field can be applied to the cells, cell derivatives, organelles, sub-cellular particles and/or vesicles, e.g., for transferring biologically active molecules such as nucleic acids or proteins into the cells, cell derivatives, organelles, sub-cellular particles and/or vesicles. To this end, the electrodes 4, 5 of base member 2 and the corresponding electrodes of the second base member establish electrode pairs, wherein the segment electrodes 4 of base member 2 and an oppositely arranged counter electrode of the second base member establish three electrode pairs while the counter electrode 5 of base member 2 and three oppositely arranged segment electrodes of the second base member also establish three electrode pairs. In this configuration the counter electrode 5 of base member 2 and the counter electrode of the second base member are each common electrodes of three segments so that the chamber 6 comprises six segments, wherein each segment is provided with one segment electrode and an area of one common counter electrode.

Two ports 7, 8 are disposed at one end 9 of the chamber 6 and two ports 10, 11 are disposed at the opposite end 12 of the chamber 6. One port of the upper ports 7, 8 can be used as inlet port for charging the chamber 6 and the other port of ports 7, 8 can be used as outlet port for discharging the chamber 6. Similarly, one port of the lower ports 10, 11 can be used as inlet port for charging the chamber 6 and the other port of ports 10, 11 can be used as outlet port for discharging the chamber 6. Accordingly, each end 9, 12 is provided with two ports 7, 8, 10, 11 through which the respective compartment of the chamber 6 can be filled with the suspension and/or through which the suspension can be purged out of this compartment. This configuration allows for simultaneous charging and discharging of the chamber 6 so that the time necessary for changing the suspension and hence the time lag between two subsequent electrical treatments of the suspension is minimized. Provision of the ports 7, 8, 10, 11 at opposite ends 9, 12 of the chamber 6 allows for easily establishing a push-pull mechanism where the suspension can be moved between the two ends 9, 12 of the chamber 6 so as to simultaneously charge one compartment at one end 9 of the chamber 6 and discharge another compartment at the opposite end 12 of the chamber 6. Accordingly, the device 1 is not a flow-through device but a device that enables charging and discharging of the chamber 6 at the same time by a push-pull mechanism wherein the liquid always leaves the chamber on the same side as it entered it.

In order to separate the suspension that has already been treated by the electric field from the suspension to be treated, a separating element 13 is provided. The separating element 13 can be moved within the chamber 6 between two terminal points 14, 15 and divides the chamber 6 into two compartments if it is in a position between the two terminal points 14, 15 as depicted in FIGS. 1b and 2c. In the exemplary embodiment depicted in FIGS. 1 and 2 the separating element 13 comprises two parts 16, 17 which are spaced from each other and flank an inner space 18 comprising a compressible material. The two spaced parts 16, 17 are wiper-like fingers so that the separating element 13 is a sealing member which provides a liquid barrier and/or gas barrier between the different compartments of the chamber 6 if it is in a position between the terminal points 14, 15 (FIGS. 1b and 2c). To this end, the separating element 13 can be made of a flexible and/or elastic material so that is also capable of compensating pressure peaks within the chamber 6. The separating element 13 may further comprise sealing lips for optimal clearing of the chamber 6. The compressible material that fills the inner space 18 may be air or any other gas, or a compressible foam or cellular material, so as to provide effective pressure compensation in the chamber 6. Accordingly, the separating element 13 also acts as a kind of cushion that balances pressure variations in the chamber 6.

The separating element 13 is coupled to an adjusting element 19 which operates and/or controls the separating element 13. That is, the separating element 13 can be moved within the chamber 6 by means of the adjusting element 19. The adjusting element 19 is disposed outside the chamber 6 so that each compartment of the chamber 6 is devoid of any interfering element that might affect the function of the device 1. The adjusting element 19 comprises a rotatable body 20 which is operatively coupled with the spaced parts 16, 17 of the separating element 13. In this exemplary embodiment the rotatable body 20 is a rotor-like element that moves the separating element 13 such that it can perform a rotational movement along the double arrow 21. This embodiment ensures precise control and constant movement of the separating element 13 within the curved chamber 6. The rotatable body 20 is surrounded by a gasket 22 sealing the adjusting element 19 against the chamber 6, wherein the rotatable body 20 is connected to the gasket 22 via spokes 23 made of an elastic material.

The device 1 further comprises a sealing inlay 24 which extends along the outer side of the chamber 6 opposite to the gasket 22 described above and seals the compartments 26 and 27 of the chamber 6 against each other. The sealing inlay 24 is made of an elastic and compressible material, e.g., silicone foam or a similar inert material, so that it enables pressure compensation within the chamber.

Figure 2A:
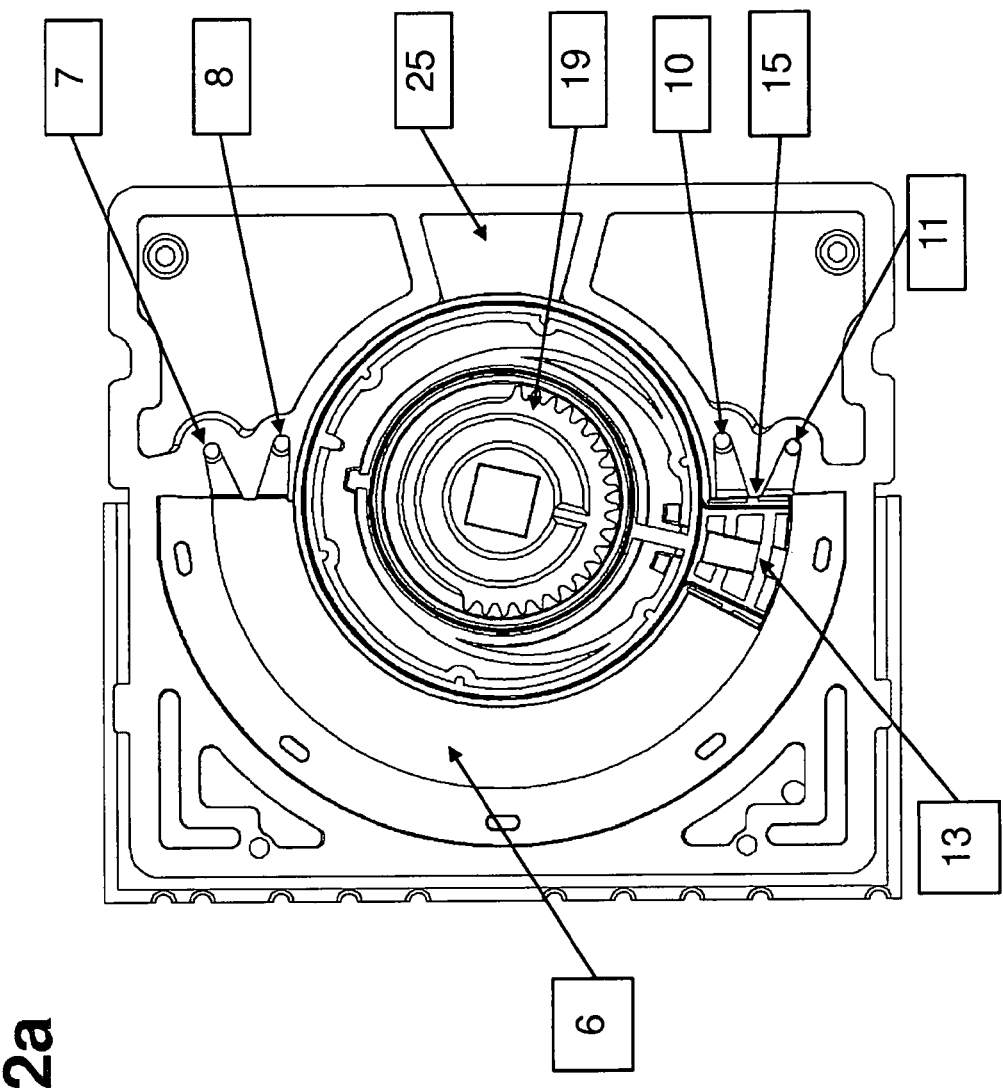
FIG. 2 shows a schematic representation of different positions of the separating element of the device according to FIG. 1.
  a) Position at a lower terminal point
  b) Position at an upper terminal point
  c) Intermediate position
  d) Parking position
Figure 2B:
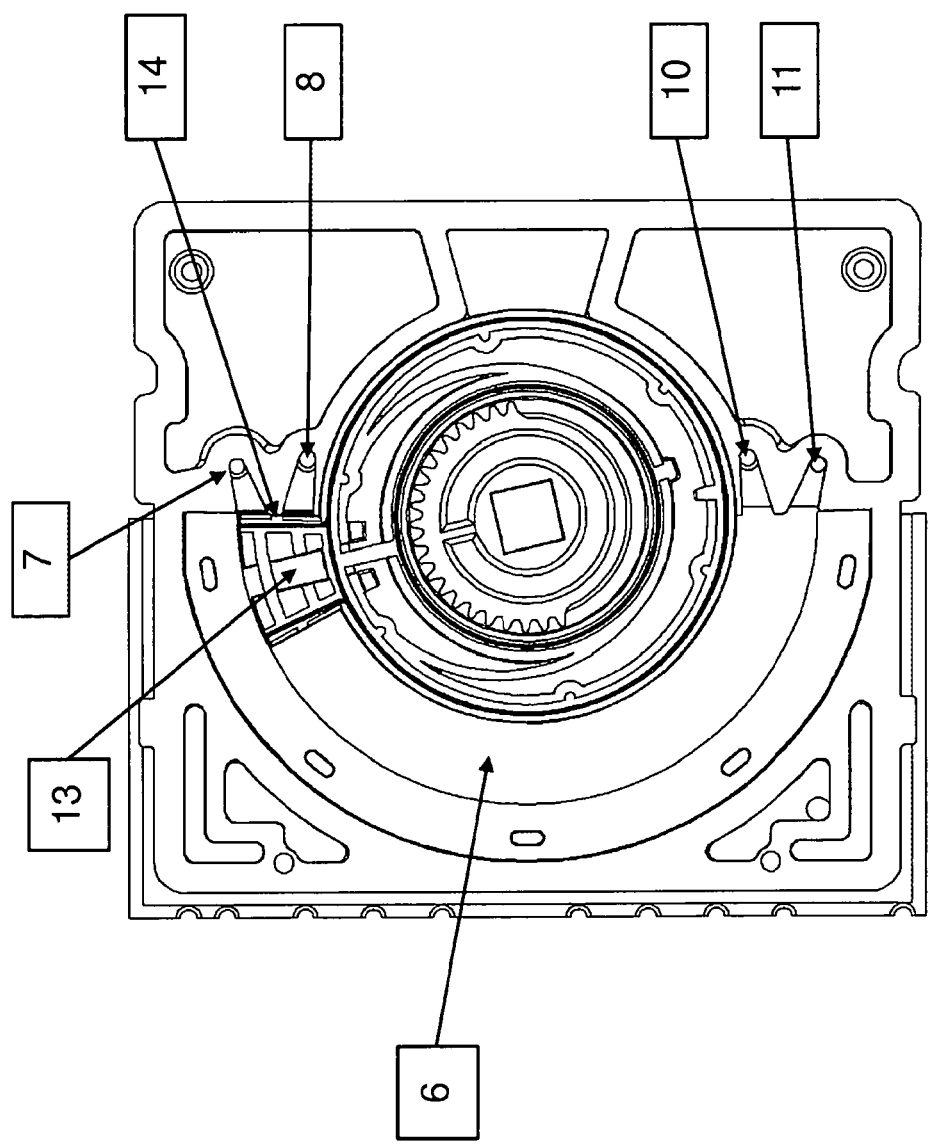
Figure 2D:
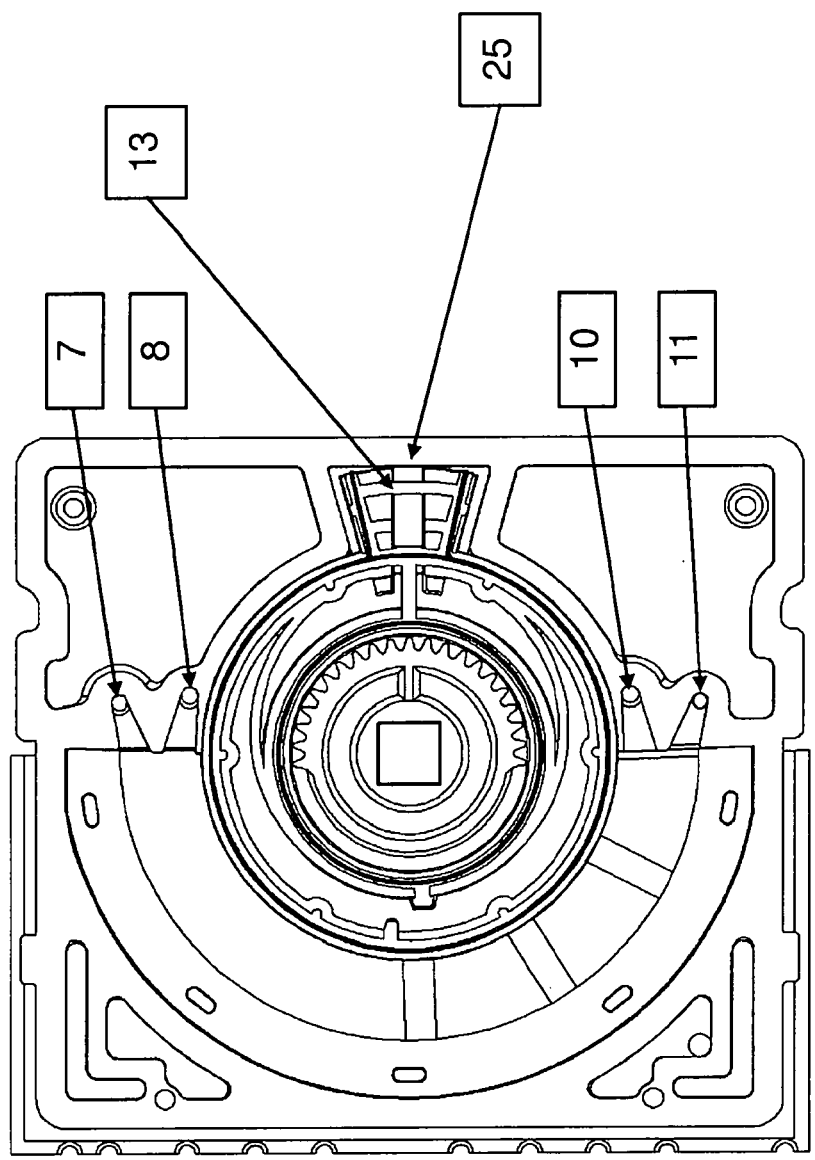

Advantageously, the device 1 includes means for fixing the separating element 13 outside the chamber 6, so that the scalable chamber 6 can be easily transformed into a static chamber 6 having a fixed volume as shown in FIG. 2d. To this end, the separating element 13 is moved by means of the adjusting element 19 to a parking site 25 where it is fixed, so as to provide the entire volume of the chamber 6 for processing of the suspension in a batch process.

FIGS. 2a-d show different positions of the separating element 13 of the device 1 according to FIG. 1. The method according to the invention is a scalable process for electrically treating a suspension of cells, cell derivatives, organelles, sub-cellular particles and/or vesicles. In FIG. 2a) the separating element 13 is set to a position at the lower terminal point 15. If the separating element 13 is rotated to a position at the upper terminal point 14 (FIG. 2b)), a first aliquot of the suspension is injected into one of the lower ports 10, 11 and thus charged into the chamber 6. The first aliquot is then processed in the chamber 6 by applying an electric field to the suspended cells, cell derivatives, organelles, sub-cellular particles and/or vesicles. Subsequently, the processed first aliquot is discharged through one of the lower ports 10, 11 by rotating the separating element 13 back to the position at the lower terminal point 15 and, at the same time, a second aliquot of the suspension is provided into one of the upper ports 7, 8 and thus charged into the chamber 6. The second aliquot is then processed in the chamber 6 by applying an electric field to the suspended cells, cell derivatives, organelles, sub-cellular particles and/or vesicles. Subsequently, the processed second aliquot is discharged through one of the upper ports 7, 8 by rotating the separating element 13 back to the position at the upper terminal point 14 and, at the same time, a third aliquot of the suspension is injected into one of the lower ports 10, 11 and thus charged into the chamber 6. The third aliquot is then processed in the chamber 6 by applying an electric field to the suspended cells, cell derivatives, organelles, sub-cellular particles and/ or vesicles. This push-pull mechanism with simultaneous charging and discharging of the suspension can be repeated until the whole suspension is treated.

The separating element 13 separates the chamber 6 in two compartments 26, 27 if it is in a position between the terminal points 14, 15 (FIG. 2c)), wherein each compartment 26, 27 of the chamber 6 is designed to hold a suspension and comprises two ports 7, 8 and 10, 11 for charging or discharging the chamber 6. Each compartment 26, 27 can receive and hold an aliquot of the suspension which is movable in and out of the chamber 6 through at the ports 7, 8 and 10, 11. The compartments 26, 27 are each further provided with one port 7, 10 through which the respective compartment 26, 27 can be filled with the suspension and with one port 8, 11 through which the suspension can be purged out of this compartment 26, 27. When the separating element 13 is rotated, one compartment 26, 27 of the chamber 6 is filled with an aliquot of the sample, while another aliquot of the sample is discharged and pushed out from the other compartment 26, 27. A container for incoming sample can be connected to an upper and a lower inlet port 7, 10 and an upper and a lower outlet port 8, 11 can be connected to a reservoir for processed sample. As becomes apparent from FIG. 2, the device 1 does not work in flow through-fashion but in a push-pull manner wherein injected sample is discharged after processing on the same side where it was charged. The chamber 6 possesses six electrode segments, one of which being always covered by the separating element 13 and thus is not usable. For example, the chamber 6 can take 834 µl per cycle. Thus, in this case, 1668 µl can be processed in a complete cycle.

In an advantageous embodiment of the invention the separating element is adjusted such that it covers exactly one or more segment electrodes so that the same electrical parameters can be established within each other electrode segment.

The static variant of the device 1 does not allow the separating element 13 to rotate. Instead the separating element 13 is fixed outside the chamber 6 at the parking site 25, not covering any electrode segment as shown in FIG. 2d. With this variant all six electrode segments can be used and thus 1000 µl sample can be processed. For example, the sample can be injected at a lower or upper inlet port 7, 10 of the device 1 and can be collected at the lower outlet port 11. Repetitive filling is not possible in this state of the device 1.

Figure 3:
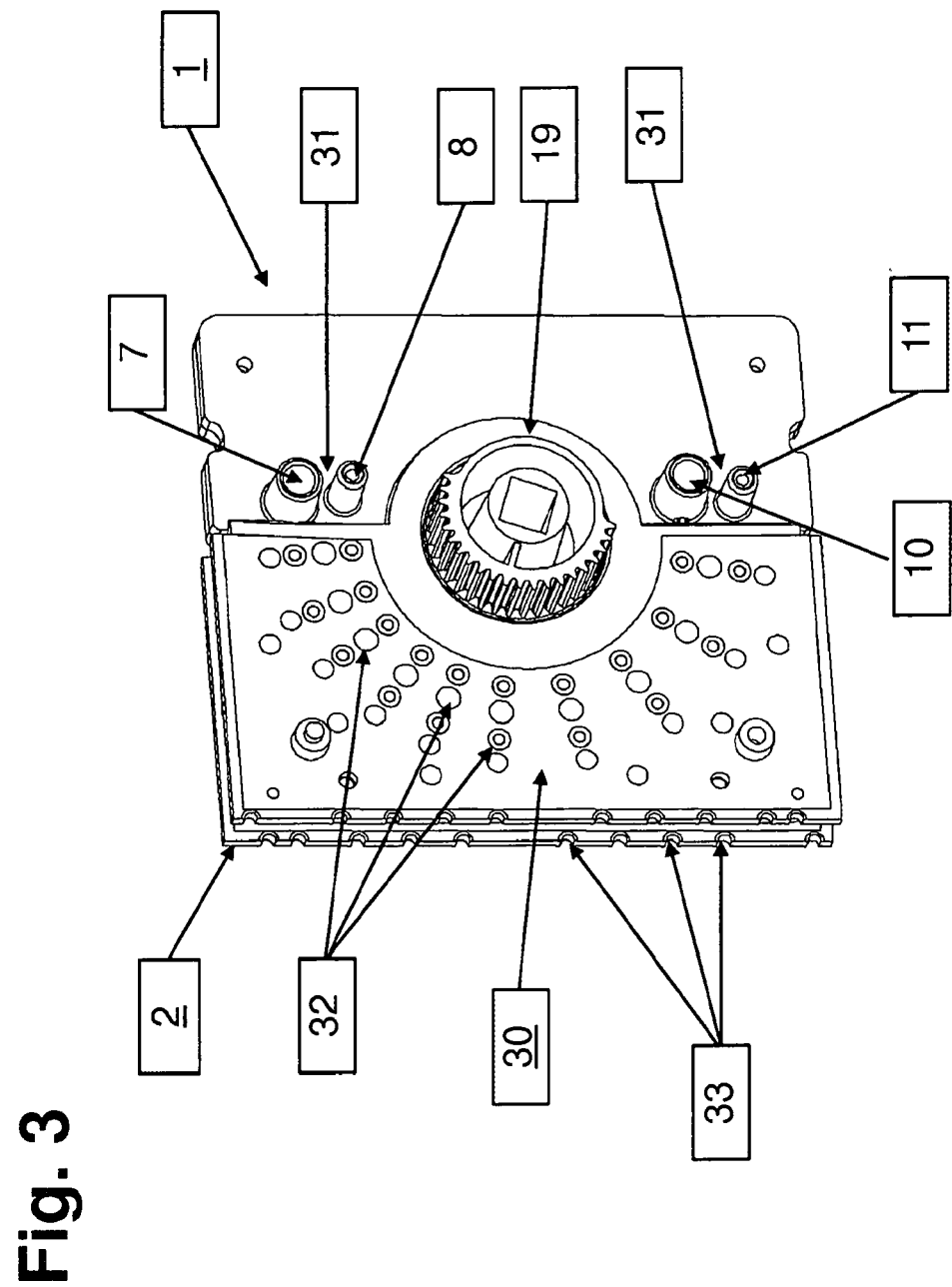
FIG. 3 shows a perspective view of the outer side of the device according to FIG. 1.

FIG. 3 shows a perspective view of the outer side of the device 1 according to FIG. 1. The device 1 comprises a base member 30, the inner side of which (not visible) being identical to the inner side of the base member 2 according to FIG. 1. The base member 30 represents a further component of the device 1 which is assembled of two components (base members 2 and 30) that are attached to each other. At its outer side, the base member 30 is provided with connectors 31 for connecting conduits to the ports 7, 8, 10, 11 of the chamber 6 according to FIGS. 1 and 2. One or more containers for the suspension to be processed and one or more reservoirs for processed suspension can be connected to the connectors 31 via suitable conduits. The suspension can be charged into and discharged from the chamber by means of a pumping element, e.g., a vacuum pump or a peristaltic pump or the like, which may be connected to the suspension circuit between the container(s)/reservoir(s) and the connectors 31. In order to render the device 1 compatible with common conduits and pumping systems, the connectors 31 can be Luer slip or Luer lock connectors.

The adjusting element 19 of the device 1 may be connected to a power unit (not shown), e.g., an electric motor, via a worm gear, a spur gear, a bevel gear, a gear rod, a belt drive, a square-bar steel, or similar gear mechanisms or power transmission elements (not shown).

The base member 30 further comprises a multitude of conductive areas 32 for providing electric connection to the electrodes in the chamber. The conductive areas 32 may comprise an electrically conductive polymer, in particular a polymer doped with electrically conductive material or an intrinsically conductive polymer. The conductive areas 32 are designed to provide an electrical connection between the electrodes and at least one electric contact point 33. In this embodiment the conductive areas 32 are holes in the base member 30 which are at least partially filled with the electrically conductive material. The conductive areas 32 are electrically coupled with at least one electric contact point 33 via at least one conductive path, e.g., copper tracks on a layer of the base member (not shown). The electric contact point can be contacted by at least one electric contact, so as to provide direct or indirect electric connection to a power source.

Figure 4:
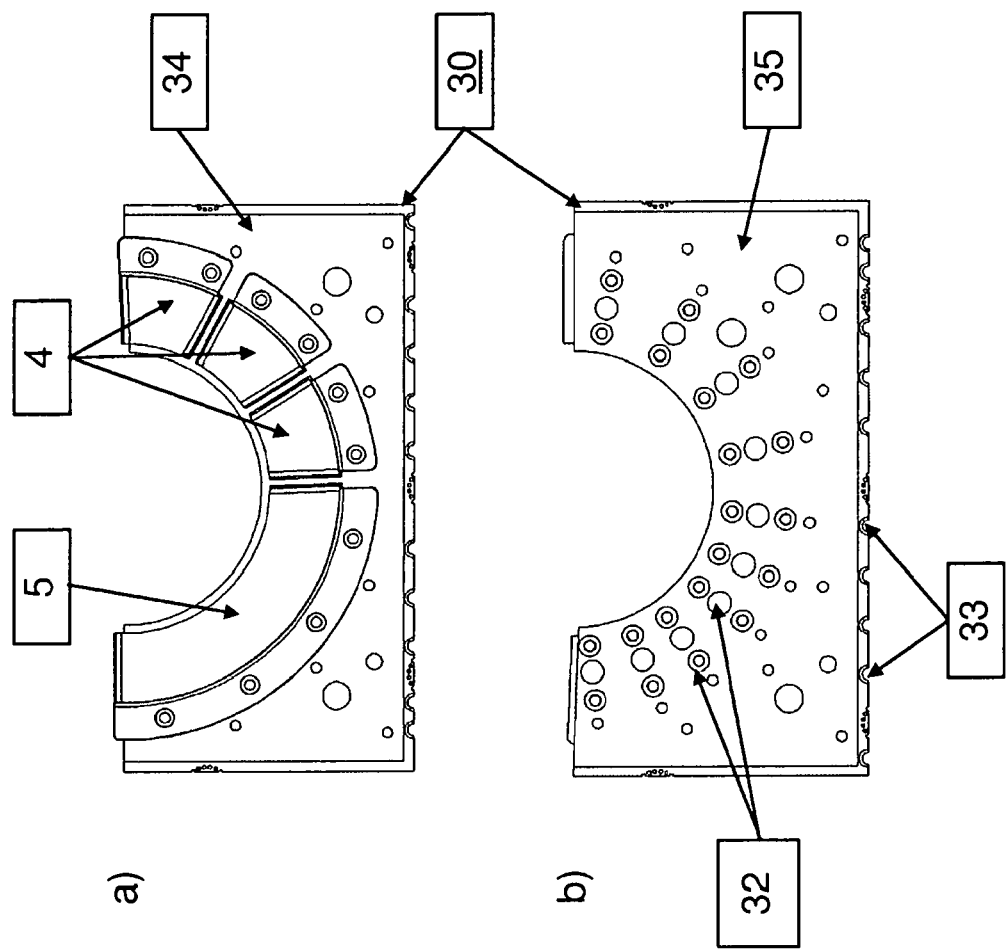
FIG. 4 shows different views of the base member according to FIG. 3.
  a) Inner side of the base member with electrodes;
  b) Outer side of the base member with conductive areas.

FIGS. 4*a* and 4*b* show different views of the base member 30 according to FIG. 3. The inner surface 34 of the base member 30 is depicted in FIG. 4*a*). Electrodes 4, 5 are attached to the inner surface 34. Three of these electrodes 4, 5 are segment electrodes 4 while one of these electrodes 4, 5 is a larger counter electrode 5. The electrodes 4, 5 are attached and connected to conductive areas 32 which extend from the inner surface 34 to the outer surface 35 of the base member 30. For example, the electrodes 4, 5 and the electrically conductive material within the conductive area 32 are made of the same material, e.g., an electrically conductive polymer, in particular a polymer doped with electrically conductive material or an intrinsically conductive polymer as described above. The polymer can be molded over the inner surface 34 and the conductive area 32 of the base member 30 and extend through holes of the conductive area 32 as shown in detail in FIG. 5*a*). The conductive areas 32 are electrically coupled with at least one electric contact point 33 via at least one conductive path (not shown). The electric contact point 33 can be contacted by at least one electric contact, so as to provide direct or indirect electric connection to a power source. In an advantageous embodiment of the invention the base member 30 is a Printed Circuit Board (PCB).

Figure 5A:
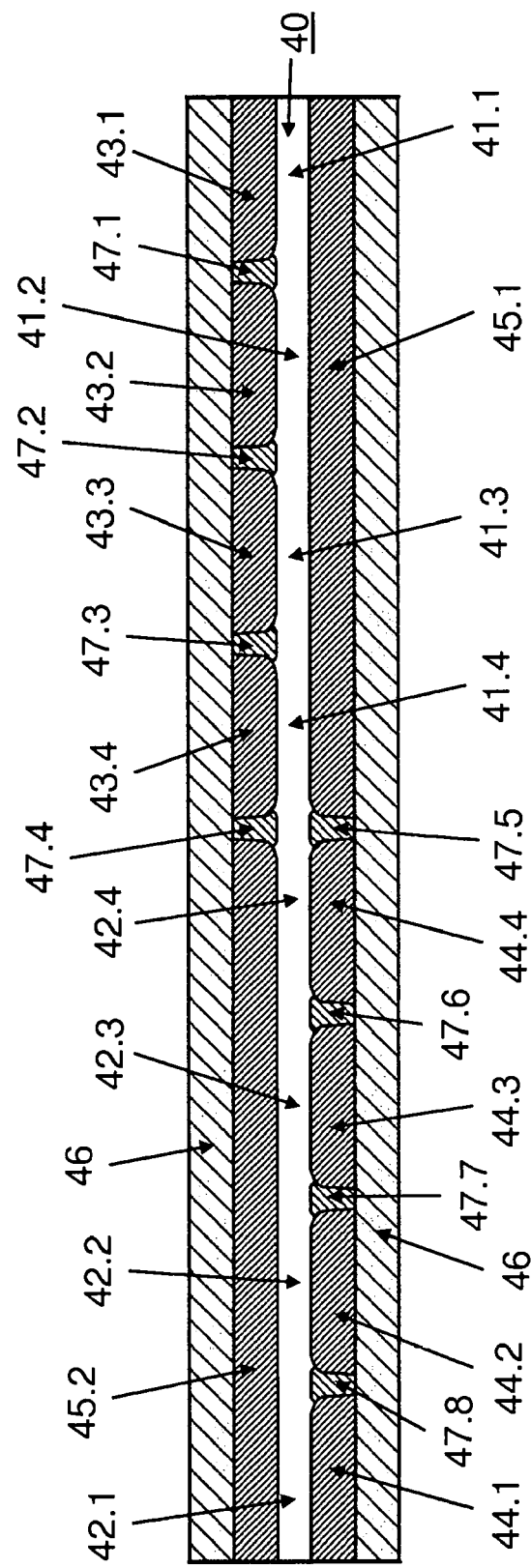
FIG. 5 shows a schematic cross-sectional view of an exemplary embodiment of a device according to the invention.
  a) Internal space comprising 8 segments;
  b) A part of the internal space according to a) comprising 2 segments.

FIG. 5*a* shows an exemplary embodiment of a part of an internal space 40 of an exemplary device according to the invention. For example, the internal space 40 may be part of the chamber 6 of the device 1 according to FIGS. 1 and 2. The internal space 40 comprises eight segments 41.1, 41.2, 41.3, 41.4, 42.1, 42.2, 42.3, 42.4, each comprising an electrode 43.1, 43.2, 43.3, 43.4, 44.1, 44.2, 44.3, 44.4. Two further electrodes 45.1 and 45.2 are disposed opposite to the electrodes 43.1, 43.2, 43.3, 43.4 and 44.1, 44.2, 44.3, 44.4, respectively. Neighboring electrodes are separated from each other by an insulating material 46 which surrounds the electrodes 43.1, 43.2, 43.3, 43.4, 44.1, 44.2, 44.3, 44.4 and fills each gap 47.1-47.8 between neighboring electrodes. The insulating material 46 may, e.g., consist of or at least comprise polycarbonate, FR4 board or other insulating materials. The characteristics of the edges of the electrodes 43.2 and 43.3 as well as the characteristics of gap 47.2 are further described in detail with reference to FIG. 5*b*. These characteristics described below may also apply to the other electrodes 43.1, 43.4, 44.1, 44.2, 44.3, 44.4 and gaps 47.1, 47.3-47.8.

Figure 5B:
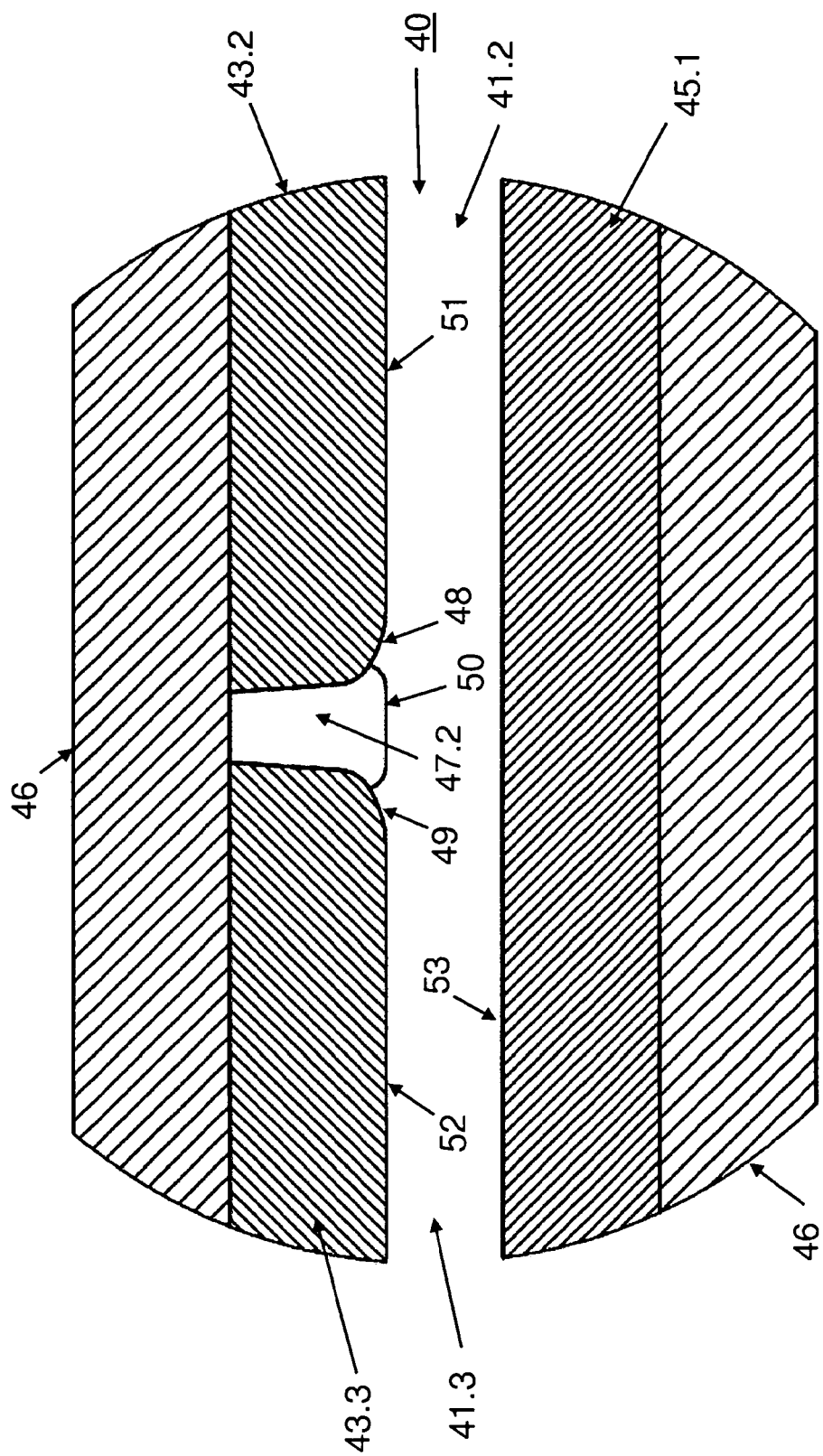

FIG. 5*b* shows a part of the internal space 40 according to FIG. 5*a* comprising two segments 41.2, 41.3 which each comprise an electrode 43.2, 43.3. A further electrode 45.1 is disposed opposite to the electrodes 43.2, 43.3. The neighboring electrodes 43.2, 43.3 are separated from each other by an insulating material 46 which surrounds the electrodes 43.2, 43.3 and fills the gap 47.2 between the neighboring electrodes 43.2, 43.3. In order to avoid undesired arcing, the edges 48, 49 of the electrodes 43.2, 43.3 facing each other within the internal space 40 are rounded. The rounded edges 48, 49 ensure a significant reduction of disturbing gradients in the electric field. Gradients in the electric field create unnecessary high local field densities and thus increase the undesired risk of arcing. Moreover, homogenization of the electric field within the internal space 40 and especially adjacent to the surface of electrodes 43.2, 43.3 can be achieved by providing a smooth shape transition from a flat electrode surface to a curved electrode surface, i.e. from a larger to a smaller fillet radius. Such electrode design further results in decreased scattering of the electric field within the internal space 40 so that the electric field lines are focused near the electrodes 43.2, 43.3.

The design of the device according to the invention may be optimized by determining the optimal ratio of the radius of each rounded edge 48, 49 and the width of the gap 47.2. This optimization is accomplished by maximizing the fillet radius of the rounded edges 48, 49 of the electrodes 43.2, 43.3 and at the same time keeping the width of the gap 47.2 as small as possible. The ideal design ensures a very low risk of arcing and a very high processing efficiency. For example, the fillet radius of the rounded edges 48, 49 of at least one of the electrodes 43.2, 43.3 could be in the range of about 0.3-2.0 mm, while the width of the gap 47.2, i.e. the distance between the neighboring electrodes 43.2, 43.3, can be in the range of about 0.5-2.0 mm.

The surface 50 of the insulating material 46 facing the internal space 40 may be formed and aligned such that it miters the surface of each of the electrodes 43.2, 43.3 in a right angle. As a result, the surface 50 of the insulating material 46 is arranged perpendicular to the surface of the electrodes 43.2 and 43.3, respectively. Due to this favorable design, the equipotential lines of an electric field within the internal space 40 meet the surface of the electrodes 43.2, 43.3 orthogonally and are therefore not deflected. Accordingly, potential inhomogeneity of the electric field can be avoided or at least moved to a region within the insulating material 46 so that the likelihood of arcing is further reduced.

The electrode 45.1 facing the electrodes 43.2, 43.3 is larger than the neighboring electrodes 43.2, 43.3 and arranged opposite to the gap 47.2. That is, no other gap is disposed opposite to the gap 47.2 so that the region near the gap 47.2 is still exposed to an electric field sufficient for efficient processing. The overall processing efficiency is therefore effectively increased. The electrode 45.1 extends over the entire length of both segments 41.2, 41.3 and thus is a common electrode of both segments 41.2, 41.3. For example, the larger electrode 45.1 may be a counter or ground electrode while the smaller electrodes 43.2, 43.3 can be either active electrodes that are set to high voltage or electrodes that are also set to ground potential. Voltage may be applied, for example, to electrode 43.2 (active electrode) while the neighboring electrode 43.3 and the counter electrode 45.1 are set to ground potential. Setting the electrodes 43.3 and 45.1 that surround the active electrode 43.2 to ground potential results in decreased scattering of the electric field within the internal space 40 so that the field lines are focused near the active electrode 43.2 and thus control of the process is enhanced.

For example, at least one of the electrodes 43.2, 43.3 may have a width in the range of 5-20 mm while the larger electrode 45 may have a width in the range of 20-80 mm.

Figure 6:
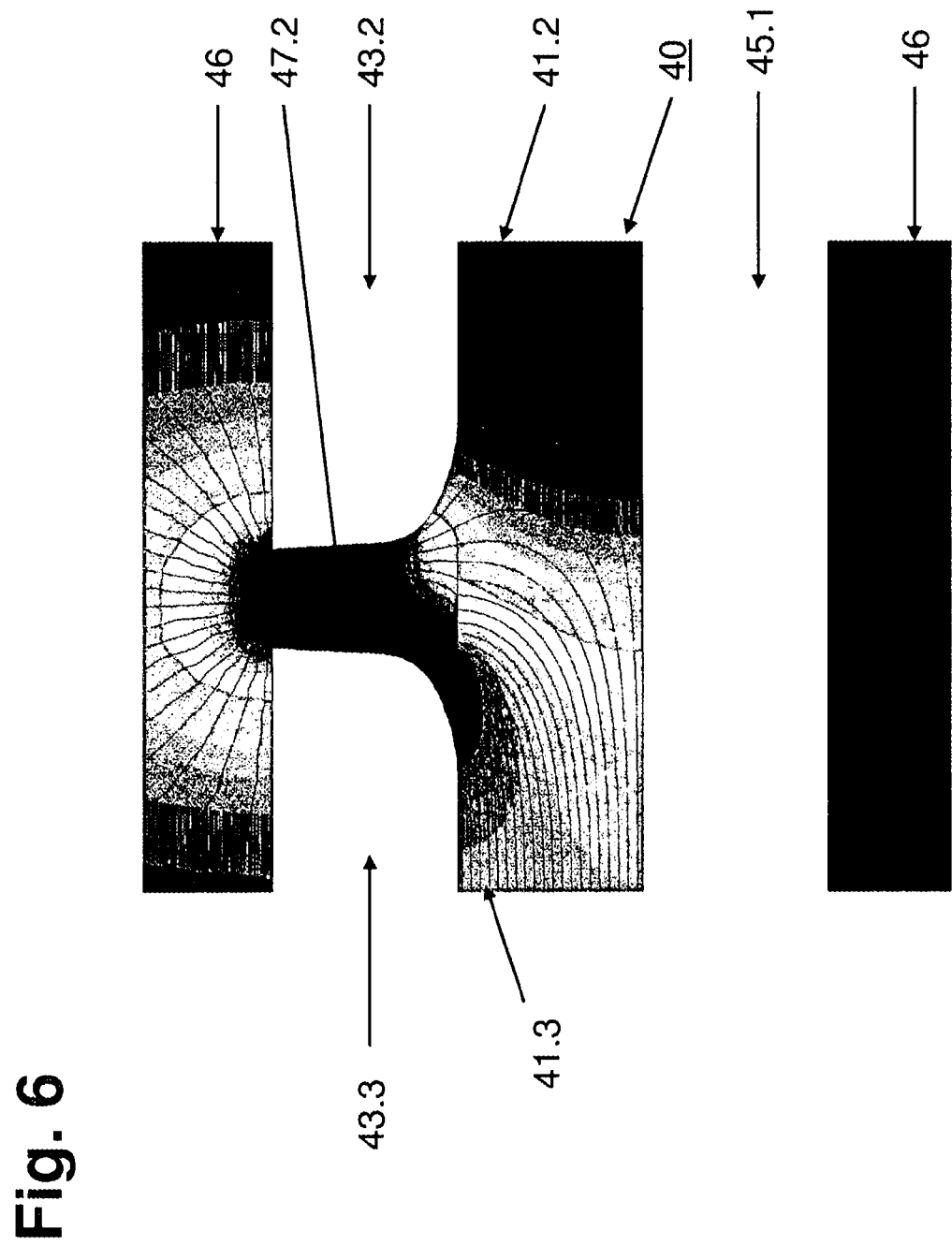
FIG. 6 shows a representation of a simulation of an electric field if high voltage is applied to the embodiment of the device according to FIG. 5.

During operation of the device according to the invention, when the suspension of cells, cell derivatives, organelles, sub-cellular particles and/or vesicles is processed by generating an electric field within the internal space 40, the flat (or, alternatively, slightly curved and/or convex) surfaces 51, 52 of the neighboring electrodes 43.2, 43.3 which are in contact with the suspension are the main active surfaces for the process. The flat surfaces 51, 52 are opposed by the larger electrode 45.1 which may be used as a counter electrode set to ground potential. For example, if high voltage is applied to electrode 43.3 and the neighboring electrode 43.2 is set to ground potential, an electric field with high field strength is generated in segment 41.3 between the parallel electrode surfaces, i.e. the flat surface 52 of electrode 43.3 and the oppositely arranged flat (or, alternatively, slightly curved and/or convex) surface 53 of electrode 45.1 (FIG. 6). Due to the advantageous design of the device according to the invention, the equipotential lines in this area are distributed homogenously so that the risk of arcing is very low. Basically, the following principle is valid: the more homogenous the distribution of the equipotential lines, the less risk of arcing. Accordingly, inhomogeneity and field gradients have to be avoided in the area of transition from the flat surface 52 to the rounded surface 49 of electrode 43.3. To this end, according to the invention a smooth and constant shape transition is ensured by the provision of a first rounding having a first, larger fillet radius and a second rounding having a second, smaller fillet radius. The second fillet radius moves the surface of electrode 43.3 away from the opposing electrode 45.1 so as to locally reduce field strength. The rounded edge 49 of electrode 43.3 and the design of the surface 50 of the insulating material 46 as described above result in a significant reduction of the risk of arcing. Moreover, the electric field is focused in segment 41.3 between the flat surface 52 of electrode 43.3 and the oppositely arranged flat surface 53 of electrode 45.1. The same applies to the neighboring electrode 43.2 if high voltage is applied to electrode 43.2 and electrode 43.3 is set to ground potential during a subsequent voltage pulse.

As becomes apparent from FIG. 6, the region near the gap 47.2 is still exposed to an electric field sufficient for efficient processing. As the volume of the suspension is processed twice when a subsequent voltage pulse is applied to electrode 43.2, medium field strength within the area between the gap 47.2 and the opposing electrode 45.1 is desired. The width of the gap 47.2, i.e. the distance between the neighboring electrodes 43.2, 43.3, is therefore optimized.

Figure 7:
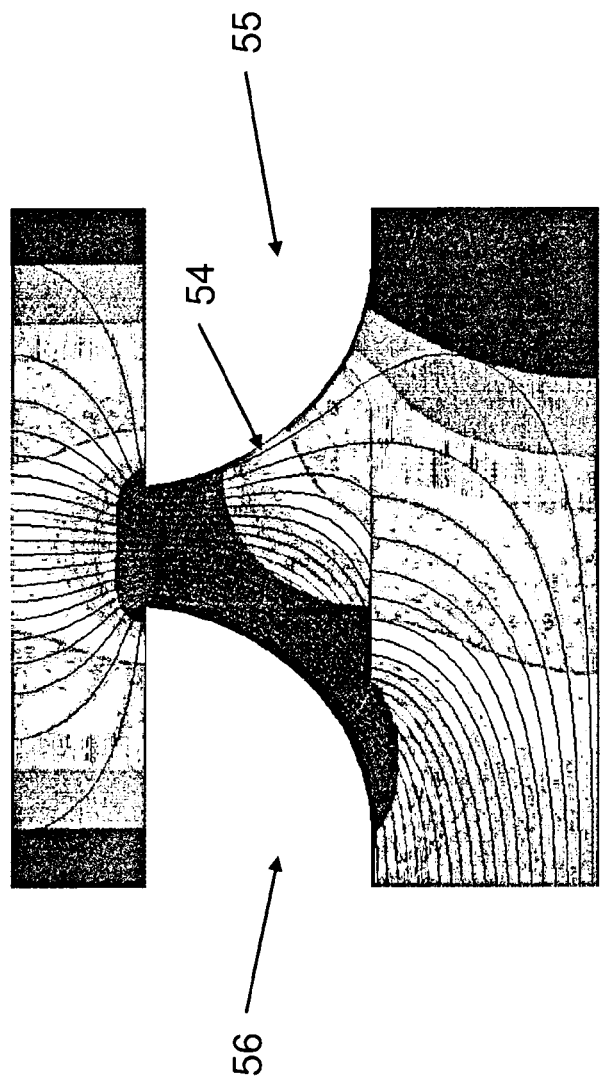
FIG. 7 shows a representation of a simulation of an electric field if high voltage is applied to a device having a larger gap and/or distance between two neighboring electrodes or electrode segments.

If the width of the gap gets too large, cells, cell derivatives, organelles, sub-cellular particles and/or vesicles in the middle of the insulating gap area are exposed to a field strength lower than half of the maximum field strength (e.g. gap 54 between electrodes 55, 56 depicted in FIG. 7). Thus, material processed twice in this area is not ideally processed.

Figure 8:
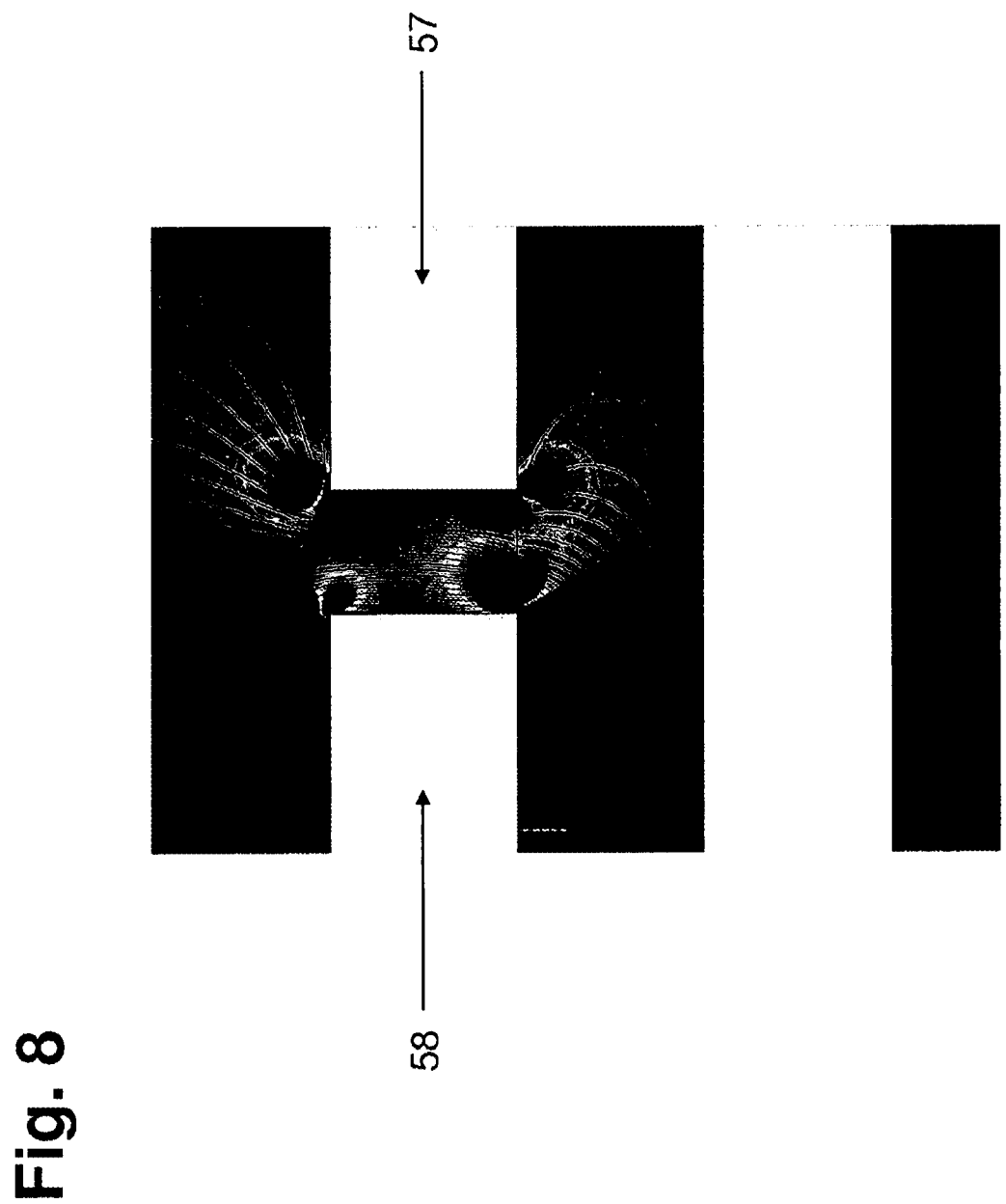
FIG. 8 shows a representation of a simulation of an electric field if high voltage is applied to a device with conventional electrode design.

The ideal design of the device according to the invention moves possible "hot spots" with very high field gradients away from the electrode surface/corners. With conventional electrode and gap design (i.e. straight, rectangular electrodes 57, 58 as depicted in FIG. 8) high field gradients close to the electrodes correlate with a low arcing threshold and thus a much higher likelihood of arcing events.

What we claim is:

1. A method for applying an electric field to a suspension of cells, cell derivatives, organelles, sub-cellular particles and/or vesicles comprising:
    applying a voltage to electrodes of a chamber comprising at least one internal space holding biologically active molecules and the suspension of cells, cell derivatives, organelles, sub-cellular particles and/or vesicles,
    the internal space comprising
    at least three segments and at least one counter electrode, wherein each segment comprises at least one segment electrode, wherein the voltage is applied to one of the segment electrodes which is active (active electrode) while all other electrodes in the internal space are set to ground potential, wherein the biologically active molecules are introduced into the living cells, cell derivatives, organelles, sub-cellular particles and/or vesicles when the electrical field is applied.

2. The method according to claim 1, wherein the voltage is applied sequentially to at least two segment electrodes or segments in the internal space.

3. The method according to claim 1, wherein the segment closest to an outlet port of the chamber is processed as a first segment in a sequence of the at least three segments followed by the segment neighboring the first segment until the last segment in the sequence, the segment most distant to the outlet port, is being processed.

4. The method according to claim 1, wherein each segment is provided with the segment electrode as an at least one first electrode and with at least one second electrode, wherein the voltage is applied to the first electrode and the second electrode is a common electrode of the at least two segments.

5. The method according to claim 2, wherein the segment closest to an outlet port of the chamber is processed as a first segment in a sequence of the at least three segments followed by the segment neighboring the first segment until the last segment in the sequence, the segment most distant to the outlet port, is being processed.

6. The method according to claim 2, wherein each segment is provided with the segment electrode as an at least one first electrode and with at least one second electrode, wherein the voltage is applied to the first electrode and the second electrode is a common electrode of the at least two segments.

7. The method according to claim 3, wherein each segment is provided with the segment electrode as an at least one first electrode and with at least one second electrode, wherein the voltage is applied to the first electrode and the second electrode is a common electrode of the at least two segments.

8. The method according to claim 1, wherein the suspension held in the at least one internal space contains said cells, cell derivatives and/or organelles.

9. The method according to claim 1, wherein field lines of the electric filed are focused proximate to the active electrode.

10. A method for applying an electric field to a suspension of cells, cell derivatives, organelles, sub-cellular particles and/or vesicles comprising:
    applying a voltage to electrodes of a chamber comprising at least one internal space holding biologically active molecules and the suspension of cells, cell derivatives, organelles, sub-cellular particles and/or vesicles, the internal space comprising at least three segments and at least one counter electrode, wherein each segment comprises at least one segment electrode, wherein the voltage is applied to one of the segment electrodes which is active (active electrode) while at least two electrodes that surround the active electrode, including the counter electrode and the segment electrodes that are not the active electrode, are set to ground potential, wherein the biologically active molecules are introduced into the living cells, cell derivatives, organelles, sub-cellular particles and/or vesicles when the electric field is applied.

11. The method according to claim 10, wherein all electrodes in the internal space, but for the active electrode, are set to ground potential.

12. A method for electroporation of cells, cell derivatives, organelles, sub-cellular particles and/or vesicles comprising:

applying a voltage to electrodes of a chamber comprising at least one internal space holding biologically active molecules and a suspension of the cells, cell derivatives, organelles, sub-cellular particles and/or vesicles, the internal space comprising at least three segments and at least one counter electrode, wherein each segment comprises at least one segment electrode, wherein the voltage is applied to one of the segment electrodes which is active (active electrode) while at least two electrodes that surround the active electrode, including the counter electrode and the segment electrodes that are not the active electrode, are set to ground potential, wherein the biologically active molecules are introduced into the living cells, cell derivatives, organelles, sub-cellular particles and/or vesicles when the electric field is applied.

13. The method according to claim 12, wherein all electrodes in the internal space, but for the active electrode, are set to ground potential.

* * * * *